United States Patent
Niermann et al.

(10) Patent No.: US 6,171,261 B1
(45) Date of Patent: Jan. 9, 2001

(54) SPECIMEN COLLECTION DEVICE AND METHOD OF DELIVERING FLUID SPECIMENS TO TEST TUBES

(75) Inventors: Volker Niermann, Little Falls; Robert S. Golabek, Jr., Towaco; Bradley Mark Wilkinson, North Haledon, all of NJ (US)

(73) Assignee: Becton Dickinson and Company, Franklin Lakes, NJ (US)

( * ) Notice: Under 35 U.S.C. 154(b), the term of this patent shall be extended for 0 days.

(21) Appl. No.: 09/369,993

(22) Filed: Aug. 6, 1999

(51) Int. Cl.[7] ........................................... A61B 5/00
(52) U.S. Cl. ........................ 600/573; 604/317; 600/577
(58) Field of Search ................................. 600/573–575, 600/577, 579; 604/317, 321, 403, 411, 415

(56) References Cited

U.S. PATENT DOCUMENTS

| | | | |
|---|---|---|---|
| 3,750,647 | 8/1973 | Gleason et al. | 128/2 F |
| 4,106,490 | 8/1978 | Spilman et al. | 128/2 F |
| 4,116,066 | 9/1978 | Mehl et al. | 73/421 R |
| 4,121,306 | 10/1978 | Bringman et al. | 4/144.2 |
| 4,258,032 | 3/1981 | Mehl | 424/148 |
| 4,300,404 | 11/1981 | Mehl et al. | 73/863.52 |
| 4,335,730 | 6/1982 | Griffin | 128/760 |
| 4,393,881 | 7/1983 | Shah | 128/760 |
| 4,492,258 | 1/1985 | Lichtenstein et al. | 141/1 |
| 4,761,379 | 8/1988 | Williams et al. | 435/296 |
| 4,769,215 | 9/1988 | Ehrenkranz | 422/58 |
| 4,895,167 | 1/1990 | Guala | 128/760 |
| 5,069,878 | 12/1991 | Ehrenkranz | 422/61 |
| 5,147,342 | 9/1992 | Kane et al. | 604/356 |
| 5,251,639 | 10/1993 | Rentsch | 128/761 |
| 5,422,076 | 6/1995 | Jones | 422/102 |
| 5,569,225 | 10/1996 | Fleury | 604/323 |
| 5,797,855 | 8/1998 | Hazard et al. | 600/513 |
| 5,849,505 | 12/1998 | Guirguis | 435/7.2 |
| 5,893,176 | 4/1999 | Magiera et al. | 4/144.4 |
| 5,894,607 | 4/1999 | Van Den Burg | 4/144.2 |
| 5,894,608 | 4/1999 | Birbara | 4/144.3 |
| 5,897,840 | 4/1999 | Owens, Jr. et al. | 422/102 |

*Primary Examiner*—Max Hindenburg (57) ABSTRACT

A specimen collection device is provided for efficient collection of biological specimens. The device includes a container with a substantially closed bottom, an open top and a side wall therebetween. An outlet aperture is provided in or near the bottom wall. An access port assembly is mounted in the outlet aperture. The access port assembly includes a split septum. The container is used with a test tube and with a cap that has a blunt cannula or blunt tube that provides access into the test tube. The blunt cannula or blunt tube can be urged through the slit in the split septum to enable a gravitational flow of the specimen from the container into the test tube. Separation of the test tube from the container allows the split septum to reseal. The test tube then can be sealed and sent to a laboratory for analysis.

24 Claims, 5 Drawing Sheets

SPECIMEN COLLECTION DEVICE AND METHOD OF DELIVERING FLUID SPECIMENS TO TEST TUBES

BACKGROUND OF THE INVENTION

1. Field of the Invention.

This invention relates to a medical collection device for collecting samples of biological fluids, such as urine, and transferring a portion of the collected fluid to a test tube for analysis.

2. Description of the Prior Art.

Biological fluids are collected periodically for laboratory analysis. The laboratory equipment that performs the analysis may only accept biological fluid stored in a test tube. However, a test tube is too small for the convenient collection of many biological fluids, such as urine. As a result, specimens often are collected in a fairly large container with a widely open top and a lid. The lid is removed to enable the biological fluid to be collected in the container. The lid then is replaced, and the container with the biological fluid is delivered to a medical technician. The technician then transfers a portion of the fluid to a test tube that can be sealed and transported to a laboratory for analysis. The transfer of the biological fluid from the collection container to the test tube is an unpleasant task that creates the risk of contaminating the specimen or contaminating the technician performing the transfer.

Some biological fluids, such as blood, are collected with assemblies that include a vacuum tube and a double ended needle cannula. One end of the needle cannula is placed in communication with the biological fluid, and the opposed end of the needle cannula is urged through a vacuum seal and into the vacuum tube. Low pressure within the vacuum tube generates a flow of the bodily fluid through the needle cannula and into the tube. Such vacuum tubes are very convenient and efficient for collecting blood samples. However, vacuum tubes have only a limited shelf life due to gradual migration of gas molecules through the walls of the tube. Additionally, sharply pointed double ended needle cannulas require careful shielding prior to, during and after use and further require special disposal precautions.

Some urine collection containers have test tubes removably connected thereto. A portion of the urine specimen collected in the container is automatically transferred to the test tube. The test tube then may be separated from the container, sealed and shipped to a laboratory for analysis. However, these prior art assemblies can lead to leakage during the initial collection of the specimen or after the separation of the test tube from the collection container.

SUMMARY OF THE INVENTION

The subject invention is directed to a specimen collection device which comprises a container having a substantially closed bottom wall, a widely open top, a bottom end and a side wall extending therebetween. Portions of the side wall adjacent the open top of the container may be formed with structure for releasably retaining a lid. For example, the side wall of the container may be formed with an array of threads that releasably engage threads on the lid.

The container is formed with an outlet aperture extending through the bottom wall or through portions of the side wall near the bottom wall. An access port is mounted in the outlet aperture. The access port comprises a pre-slit septum that may be formed from a resilient elastomeric material. The pre-slit septum is retained in a condition where the slit normally is sealingly closed to prevent an outflow of liquid from the container. However, the resilient elastomeric material of the septum enables a blunt cannula or tube to be urged through the slit for accessing liquid in the container. The septum will resiliently return to its initial sealed condition when the blunt cannula or tube is removed from the access port, to again prevent leakage of liquid from the container.

The septum may initially be mounted in a mounting collar, which in turn is mounted in the outlet aperture of the container. The mounting collar may be a substantially cylindrical structure having a barb or an array of barbs thereon. The barbs may deform or generate deformation of the container during insertion of the mounting collar into the outlet aperture. After sufficient insertion, however, the barbs may pass through the outlet aperture, thereby enabling both the mounting collar and the container to return to their undeformed condition in which the barbs lockingly retain the mounting collar and the pre-slit septum in the outlet aperture of the container.

The device may further comprise a test tube for receiving a portion of the liquid specimen from the container. The test tube typically will be significantly smaller than the container, and includes a closed bottom, an open top and a side wall extending therebetween.

The device further includes a cap for placing the test tube in communication with the container. The cap may be configured for releasable engagement with portions of the side wall of the test tube adjacent the open top. The cap may further include a transverse wall configured to extend substantially across the open top of the test tube. The transverse wall is formed with an inlet aperture that is eccentric to the transverse wall and a vent aperture. An inlet conduit extends rigidly upwardly from and eccentric to the transverse wall and is registered with the inlet aperture. The inlet conduit is dimensioned and configured to be urged through the pre-slit septum for providing communication between the container and the test tube. The inlet conduit may include a tapered end to facilitate movement through the pre-slit septum.

The cap may further include a vent conduit extending from the vent aperture into the test tube. The vent conduit functions to permit an outflow of air as the liquid flows into the test tube. The vent conduit further comprises a bottom wall having a narrow slit. A sufficient volume of liquid in the test tube will cover the bottom wall of the vent conduit, and will thereby prevent further escape of air from the test tube. This inability to vent air from the test tube will impede and eventually stop the flow of liquid through the inlet conduit and into the test tube. The bottom wall of the vent conduit may be adjusted a distance form the closed bottom of the test tube to selectively elect the amount of fluid to be transferred from the container to the test tube.

The cap may further include a cylindrical cover wall extending from transverse wall and surrounding the inlet conduit. A cover may be hinged to the cylindrical cover wall and may be movable into sealing engagement with the cover wall.

The specimen collection device is used by initially depositing a sample of biological fluid, such as urine, into the container. The pre-slit septum will prevent an outflow of the collected specimen from the outlet aperture of the container. The lid then may be removably mounted over the open top of the container, and the container may be delivered to a medical technician. The technician employs the above-described assembly of a test tube and cap assembly. In particular, the cover of the cap is rotated away from sealed engagement with the inlet conduit. The end of the inlet conduit then is urged through the pre-slit septum to access the contents of the container. Fluid in the container will flow through the inlet conduit and into the test tube. The volume of fluid in the test tube eventually will rise to the level of the bottom wall of vent conduit. Liquid in the test tube then will prevent further venting of air through the narrow slit from the test tube and will stop the inflow of fluid through the inlet conduit and into the test tube. The technician then merely separates the assembled test tube and cap from the collection container. As the inlet conduit is removed from the pre-slit septum, the septum will return to its initial configuration and will sealingly close the outlet aperture in the container. The cover of the cap may be rotated into sealing engagement with the cover wall of the cap. The sealed test tube then may be transported to a laboratory for analysis. Once the cover of the cap is sealed it cannot be re-opened. The access to the specimen in the test tube is only obtained by twisting the cap off the test tube.

The container may be accessed a second time, if necessary, to obtain a second specimen for analysis. Alternatively, the container may merely be discarded. It will be appreciated that no part of the system employs sharps that require special handling or special disposal. As a result, the container may be discarded substantially in the manner of a used diaper. Similarly, the test tube and cap assembly can be discarded in a conventional receptacle upon completion of the laboratory analysis on the specimen.

DETAILED DESCRIPTION

While this invention is satisfied by embodiments in many different forms, there will herein be described in detail a preferred embodiment of the invention with the understanding that the present disclosure is to be considered as exemplary of the principles of the invention and is not intended to limit the invention to the embodiments illustrated and described. The scope of the invention will be measured by the appended claims and their equivalents.

Figures 1, 2:
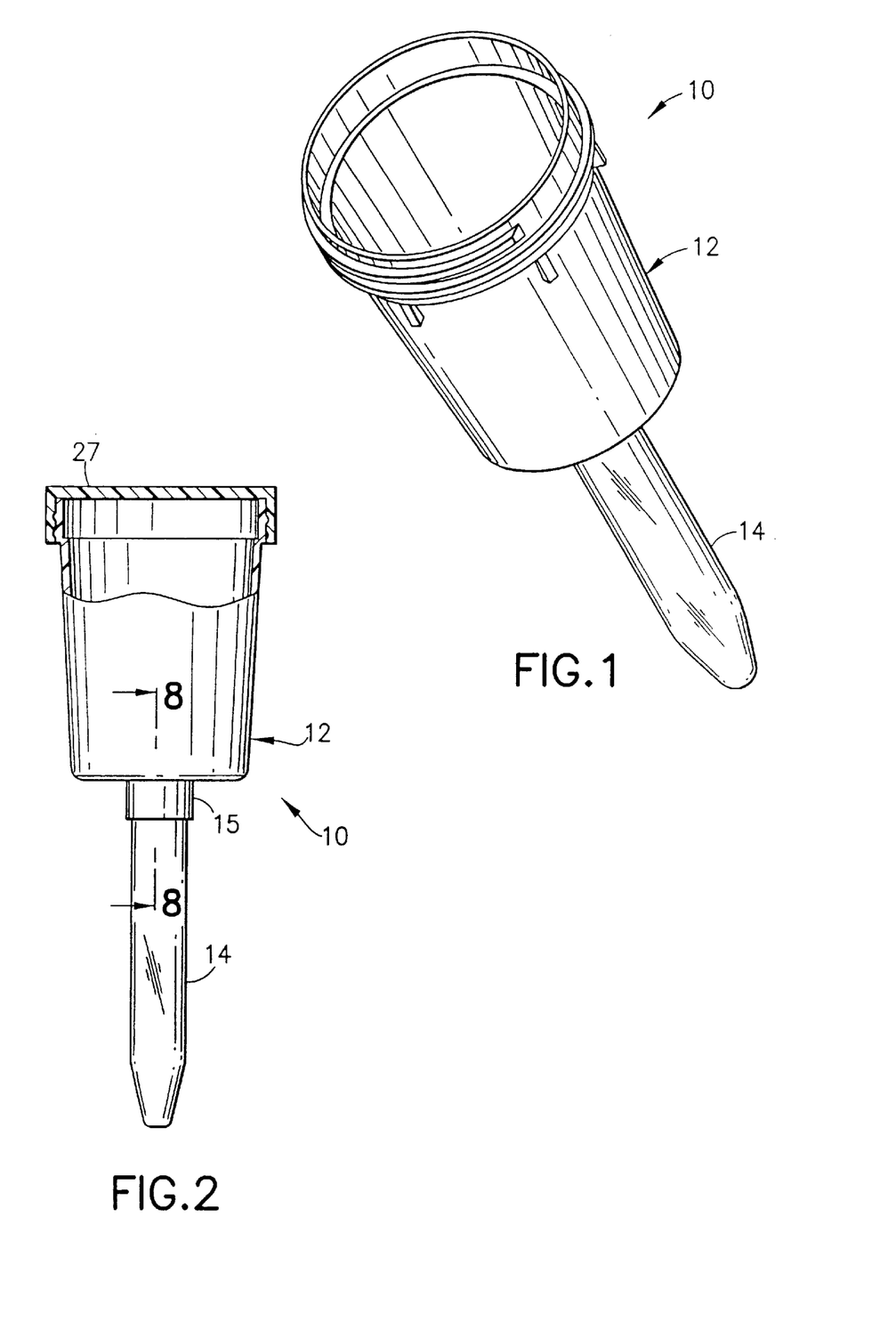
FIG. 1. is a perspective view of a system in accordance with the subject invention.
FIG. 2 is a side elevational view partly in section of the system with the lid attached.
Figure 4:
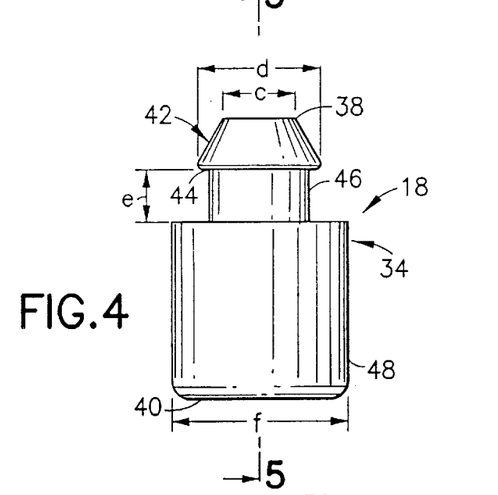
FIG. 4 is a side elevational view of the container access port assembly of the subject system.
Figure 5:
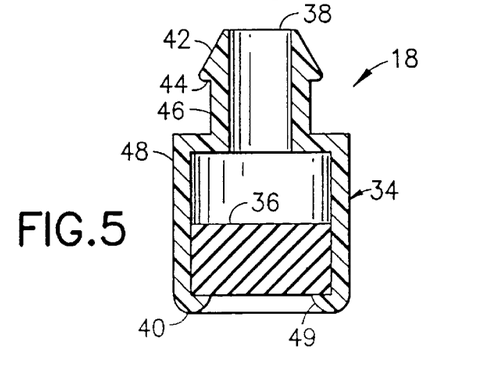
FIG. 5 is a cross-sectional view taken along line 5—5 in FIG. 4.

A specimen collection device for collecting bodily fluids and in accordance with the subject invention is identified generally by the numeral 10 in FIGS. 1 and 2. Specimen collection device 10 includes a container 12, a test tube 14 and a cap 15, as shown in FIGS. 1 and 2. Specimen collection system 10 also includes an access port assembly 18 as shown in FIGS. 4 and 5 and as discussed in greater detail below.

Figure 3:
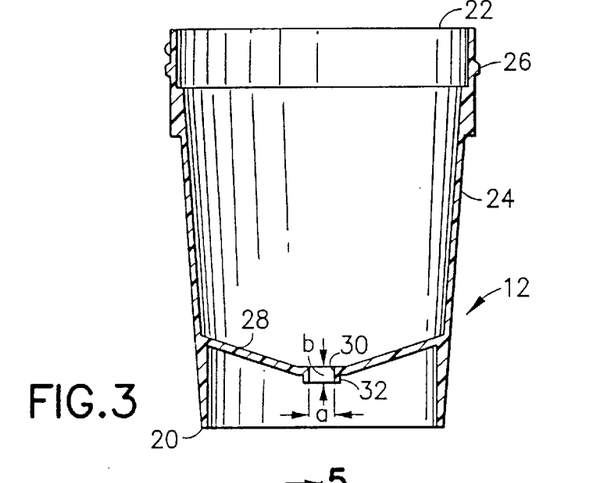
FIG. 3 is a longitudinal cross-sectional view of the collection container of the system shown in FIGS. 1 and 2.

With reference to FIG. 3, container 12 is unitarily molded from a plastic material and includes a bottom end 20, a widely open top 22 and a generally frustum-shaped side wall 24 extending continuously between bottom end 20 and open top 22. Side wall 24 includes an array of external threads 26 in proximity to open top 22. Threads 26 are dimensioned and configured to releasably engage lid 27 (shown in FIG. 2) for storage and transportation of a specimen deposited into container 12. There are other methods known by one skilled in the art to mount lid 27 on open top 22 which include but are not limited to snap fits, adhesives, fasteners, and heat or ultrasonic welding methods. In addition, the present invention is not limited to having lid 27 close open top 22. There are many ways known by one skilled in the art to close open top 22 which include but are not limited to heat or ultrasonic welding side walls 24 together, incorporating snap fits on side walls 24 to lock side walls 24 together, and utilizing an adhesive to close open top 22 and bond side walls 24 together.

Container 12 further includes a substantially conically dished bottom wall 28 that extends unitarily across portions of frustum-shaped side wall 24 between bottom end 20 and open top 22. Bottom wall 28 is substantially symmetrical with frustum-shaped side wall 24 and is oriented to have its concave surface facing upwardly toward open top 22. An outlet aperture 30 of diameter "a" extends centrally through bottom wall 28 at the gravitational low point. Alternatively, the outlet aperture 30 may be on lid 27. In this embodiment, device 10 would have to be inverted to fill tube 14.

A short cylindrical nipple 32 of length "b" is defined unitarily in bottom wall 28 at outlet aperture 30. Thus, nipple 32 defines the lowest portion of bottom wall 28. However, nipple 32 is disposed above bottom end 20 of container 12. Thus, when bottom end 20 of container 12 is supported on a surface, nipple 32 will be spaced above the surface.

Access port assembly 18 comprises a stepped tubular mounting collar 34 and a split septum 36 as shown in FIGS. 4 and 5. More particularly, collar 34 is unitarily molded from a plastic material and includes opposed top and bottom ends 38 and 40, respectively. Portions of collar 34 adjacent top end 38 define a frustum-shaped mounting barb 42 having a minor diameter "c" adjacent top end 38 that is less than diameter "a" of outlet aperture 30 of container 12. However, mounting barb 42 defines a maximum diameter "d" at locations spaced from top end 38 of collar 34. Diameter "d" on mounting barb 42 exceeds diameter "a" of outlet aperture 30 in collection container 12. Mounting barb 42 includes a locking shoulder 44 which is aligned orthogonally to the axis of collar 34 and which faces bottom end 40 of collar 34. Locking shoulder 44 will be positioned adjacent to the upper face of dished bottom wall 28 of container 12 in order to lock collar 34 to container 12 as explained herein.

Mounting collar 34 further includes a narrow neck portion 46 which has an outside diameter approximately equal to diameter "a" of outlet aperture 30 of container 12. Additionally, neck 46 defines a length "e" approximately equal to or slightly greater than length "b" of nipple 32 on container 12.

A substantially hollow tubular septum retainer 48 is defined on mounting collar 34 and extends from bottom end 40 to tubular neck 46. Septum retainer 48 defines an outside diameter "f" which exceeds the inside diameter "a" of outlet aperture 32. Hence, septum retainer 48 prevents mounting collar 34 from being forced entirely through outlet aperture 30. Portions of septum retainer 48 adjacent bottom end 40 of mounting collar 34 include an inwardly projecting lip 49 for trapping the septum. Split septum 36 is contained in a resiliently compressed state within septum retainer 48. Split septum 36 includes a diametrically aligned slit which enables access by a blunt cannula or tube as explained further herein.

Split septum 36 may also be mounted directly on container 12 without the use of tubular mounting collar 34 or any other secondary component. This alternative embodiment can be done by molding split septum 36 directly into outlet aperture 30, simply mounting septum 36 in outlet aperture 30. The molding of split septum 36 could be accomplished by a two material injection molding process that it well known to those skilled in the art.

Figures 6, 7, 7A:
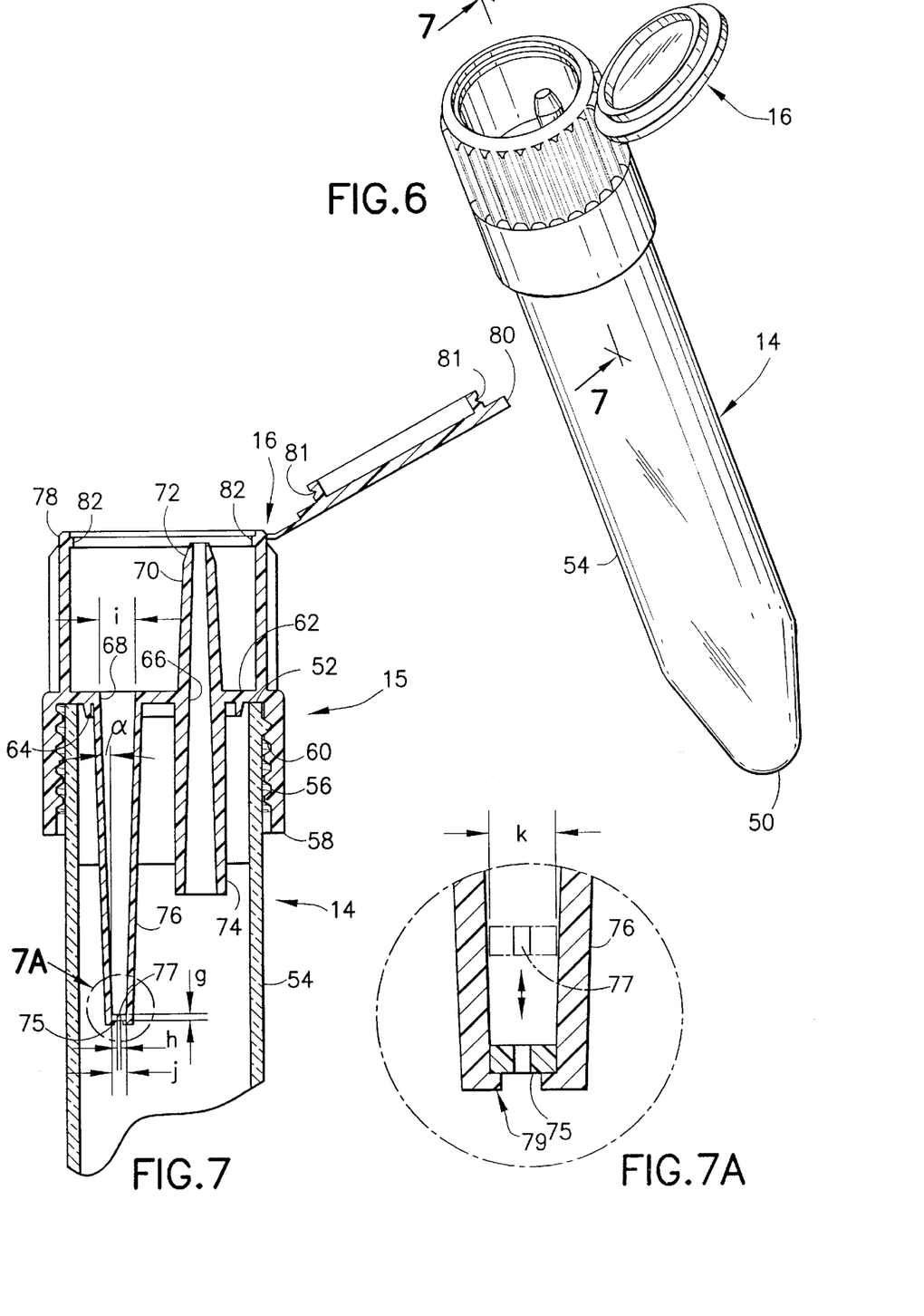
FIG. 6 is a perspective view of the test tube and cap assembly of the subject system.
FIG. 7 is a cross-sectional view taken along line 7—7 in FIG. 6.
FIG. 7A is an enlarged view of FIG. 7.
Figure 8:
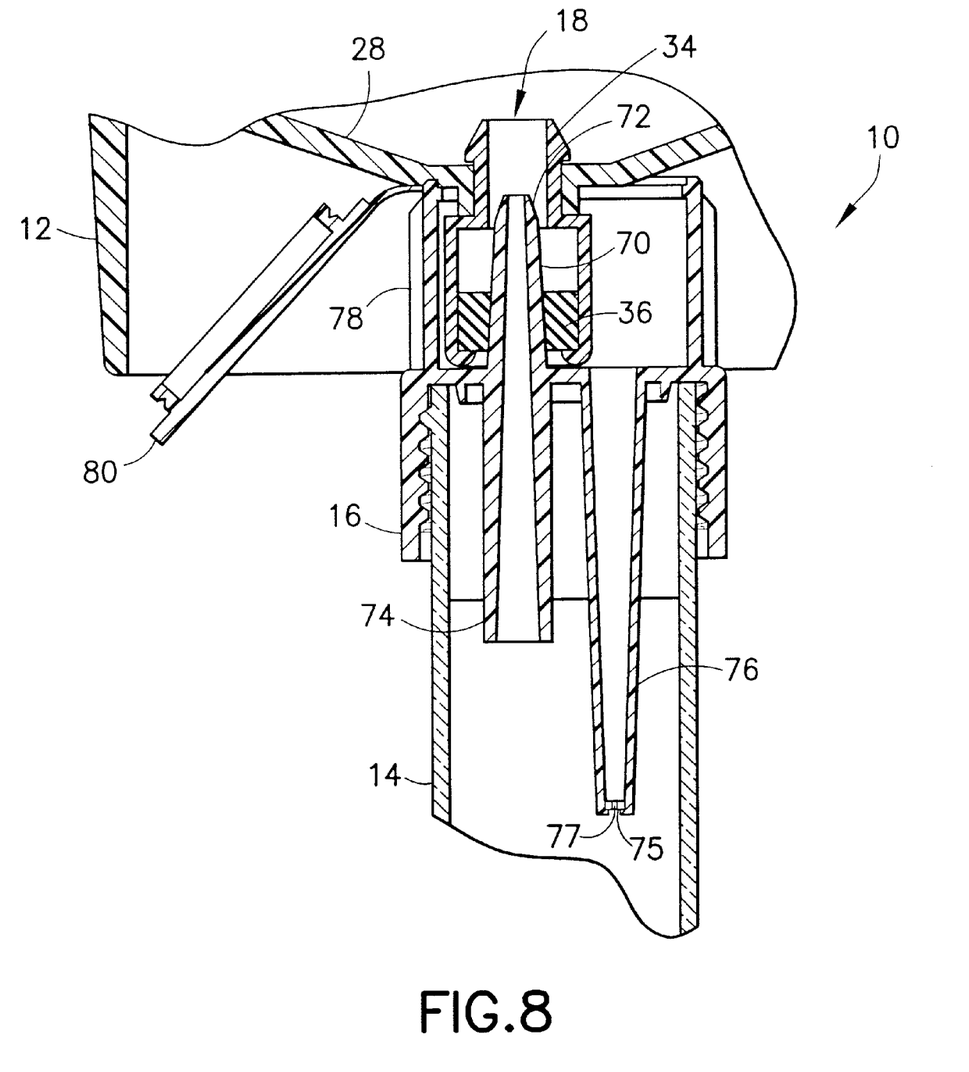
FIG. 8 is a cross-sectional view taken along line 8—8 in FIG. 2.

Test tube 14 and cap 16 of device 10 are illustrated in greater detail in FIGS. 6 and 7. More particularly, test tube 16 includes a closed bottom end 50, an open top end 52 and a cylindrical side wall 54 extending therebetween. Portions of side wall 54 in proximity to open top 52 are provided with an array of external threads 56.

Cap 16 is unitarily molded from a thermoplastic material and includes a generally cylindrical mounting wall 58 having an array of internal threads 60 that are dimensioned and configured for mating with external threads 56 on test tube 14. Cap 16 further includes a transverse wall 62 extending orthogonally across cylindrical mounting wall 58. Transverse wall 62 is provided with an annular sealing wall 64 projecting downwardly a short distance from transverse wall 62 and spaced concentrically inwardly from cylindrical mounting wall 58. Annular sealing wall 64 is dimensioned to closely engage inner circumferential portions of side wall 54 on test tube 14 adjacent open top 52 thereof when cylindrical side wall 58 of cap 16 is threaded into engagement with test tube 14.

Transverse wall 62 is further formed with an inlet aperture 66 and a vent aperture 68. Inlet aperture 66 and vent aperture 68 both preferably are offset from the axis about which cylindrical mounting wall 58 of cap 16 is generated. For example, inlet aperture 66 is eccentric to and exactly through transverse wall 62. This geometry allows cap 16 to be offset from access port assembly 18 to provide clearance for vent aperture 68. An upper inlet conduit 70 extends unitarily and rigidly upwardly from transverse wall 62 and in registration with inlet aperture 66. Inlet conduit 70 is eccentric to transverse wall 62 for the same purpose described above. Upper inlet conduit 70 provides communication with inlet aperture 66 and with interior portions of test tube 14. Upper inlet conduit 70 includes a taper 72 at the end remote from transverse wall 62. Taper 72 provides easier access through septum 36 of access port assembly 18. A lower inlet conduit 74 projects downwardly a selected distance from transverse wall 62 and is registered with upper inlet conduit 70. Thus, upper and lower inlet conduits 70 and 74 both communicate with inlet aperture 66 and provide communication into test tube 14.

A vent conduit 76 extends downwardly from transverse wall 62 and is registered with vent aperture 68. Vent conduit 76 includes a bottom wall 75. Vent conduit 76 has an inside taper "α" such that an inside diameter "i" of vent conduit 76 planar to transverse wall 62 is larger than the inside diameter "j" below transverse wall 68. Bottom wall 75 has a thickness "g" and a width "k". Bottom wall 75 includes a narrow slit 77 with a diameter "h" and a length equivalent to bottom wall thickness "g". Narrow slit 77 permits a venting of air from test tube 14 as liquid flows through upper and lower inlet conduits 70 and 74. Narrow slit 77 has a diameter "h" which is about 0.010" and a length diameter about 0.020" to about 0.030. " This geometry of narrow slit 77 facilitates venting of air through vent conduit 76 and prevents liquid from flowing out into vent conduit 76 by capillary action. Taper "α" of vent conduit 76 provides a divergent section for the air flow from narrow slit 77. The flow of air entering taper "α" reduces in velocity and regains pressure in accordance with the Bernoulli equation. This feature allows a steady flow of fluid into test tube 14.

Vent conduit 76 may also include a lip portion 79 which supports bottom wall 75 at the bottom of vent conduit 76. Bottom wall 75 is adjustable such that various diameters of bottom wall 75 may be inserted in vent conduit 76. The bottom wall 75 will be in various height locations relative to closed bottom 50 of the test tube 14 depending on the diameter of bottom wall 75. A frictional fit between bottom wall 75 and vent conduit 76 based on taper "α" would hold bottom wall 75 in place. It is preferred to have bottom wall secured to vent conduit 76. There are many ways to secure these components known by one skilled in the art which are all included within the scope of this invention. It is most preferred to have bottom wall 75 and vent conduit 76 a unitary structure. The height of bottom wall 75 relative to closed bottom 50 would be selectively elected based on the amount of fluid desired to be transferred from container 12 to test tube 14. The structure would then be manufactured. It is the distance from bottom wall 75 to closed bottom 50 of test tube 14 that is adjustable and determines the quantity of a biological sample collected in test tube 14. This desired quantity is independent of the length of vent conduit 76. By providing various heights of bottom wall 75, various quantities of the fluid in test tube 14 are available independent of the length of vent conduit 76.

A cylindrical cover wall 78 extends upwardly from transverse wall 62 beyond upper inlet conduit 70. A cover 80 is hinged to cover wall 78 and can be rotated into sealed engagement with cover wall 78. This provides a permanent and leak preventative seal. When actuated, the fluid in test tube 14 is only accessible by unscrewing cap 15.

Specimen collection device 10 is placed in condition for use by mounting access port assembly 18 into outlet aperture 30 of container 12. This mounting of access port assembly 18 to container 12 typically will be carried out by the manufacturer of system 10 and prior to sale to a customer. More particularly, the small diameter end of mounting barb 42 is urged into outlet aperture 30. The tapered configuration of mounting barb 42 generates an outward deflection of portions of nipple 32 surrounding and defining outlet aperture 30 and a simultaneous inward deflection of mounting barb 42. After sufficient movement of access port assembly 18 into mounting aperture 30, mounting barb 42 will pass upwardly beyond bottom wall 28 thereby enabling all parts to resiliently return to an undeformed condition and enabling locking shoulder 44 of mounting barb 42 to lockingly engage portions of bottom wall 28 surrounding outlet aperture 30 of container 12. The tight interfit between mounting collar 34 and nipple 32 of container 12 will prevent leakage of fluid therebetween. Additionally, split septum 36 provides a liquid-tight seal within mounting collar 34 of axis port assembly 18.

Container 12 with access port assembly 18 mounted therein can be used by a patient for collection of a biological fluid, such as urine. Container 12 then can be temporarily sealed with a lid 29 (see FIG. 2) engaged with threads 26 on portions of side wall 24 of container 12 adjacent open top 20. Container 12 with the fluid therein can be delivered by the patient to a medical technician.

A portion of the fluid in container 12 can be transferred to test tube 14 by the medical technician. More particularly, cover 80 of cap 15 can be hingedly rotated away from cylindrical cover wall 78 to expose upper inlet conduit 70. Tapered end 72 of upper inlet conduit 70 then can be urged through the slit in split septum 36. As upper inlet conduit 70 is urged through split septum 36, the elastomeric material from which septum 36 is formed will closely surround upper inlet conduit 70 to prevent leakage between upper inlet conduit 70 and septum 36. However, the interior of upper inlet conduit 70 will be placed in communication with fluid in container 12. Hence, a flow of fluid from container 12 to test tube 14 is enabled. Air that had been in test tube 14 can be vented through narrrow slit 77 of vent conduit 76. However, after a sufficient volume of fluid has entered test tube 14, bottom wall end 75 of vent conduit 76 and narrow slit 77 will be covered, thereby preventing further venting and impeding additional flow of fluid into test tube 14. The medical technician then may merely pull the assembly of test tube 14 and cap 16 out of split septum 36. Portions of septum 36 on opposite sides of the slit will close together due to the inherent resiliency of septum 36. Test tube 14 can be sealed by merely rotating cover 80 about the hinged connection to cylindrical cover wall 78 for sealing cap 16 and test tube 14. Snap fit 81 of cover 80 attached to fitting 82 of cover wall 78 to provide a permanent seal. Cover 80 seals cover wall 78 and test tube 14 while providing leak prevention of the fluid in test tube 14. Inlet conduit 72 may be sealed by cover 80 to provide additional leak prevention.

The assembly of test tube 14 and cap 16 with the fluid specimen therein then can be transported to a laboratory for analysis. If necessary, an additional specimen can be obtained for analysis merely by placing a new test tube 14 and cap 16 assembly into communication with container 12 as described above. Access to test tube 14 can only be accomplished by twisting cap 15 off test tube 14 after snap fit 81 is attached to fitting 82. This safety feature provides additional protection against contact with the fluid in test tube 14. Container 12 can be discarded in an appropriate sanitary receptacle, such as a trash receptacle that might be used for a soiled diaper. A special sharps receptacle is not required. Similarly, the assembly of test tube 14 and cap 16 can be discarded in a conventional receptacle after completion of laboratory analysis. Once again, a sharps receptacle disposal is not required because no sharp implements are present.

Figure 9:
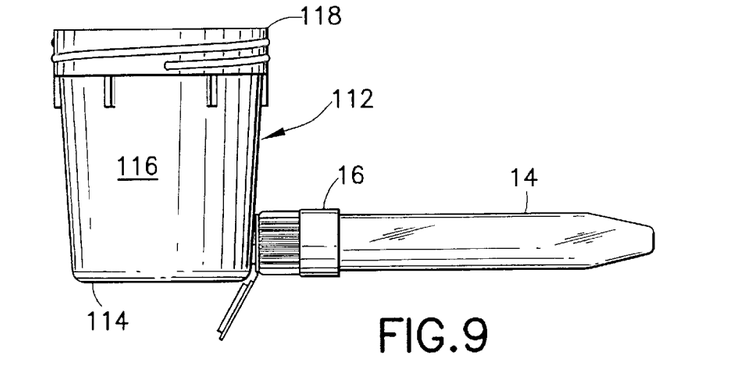
FIG. 9 is a side elevational view of an alternate embodiment.
Figure 10:
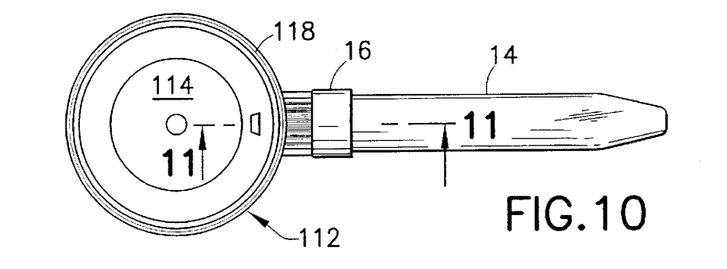
FIG. 10 is a top plan view of the system shown in FIG. 9.
Figure 11:
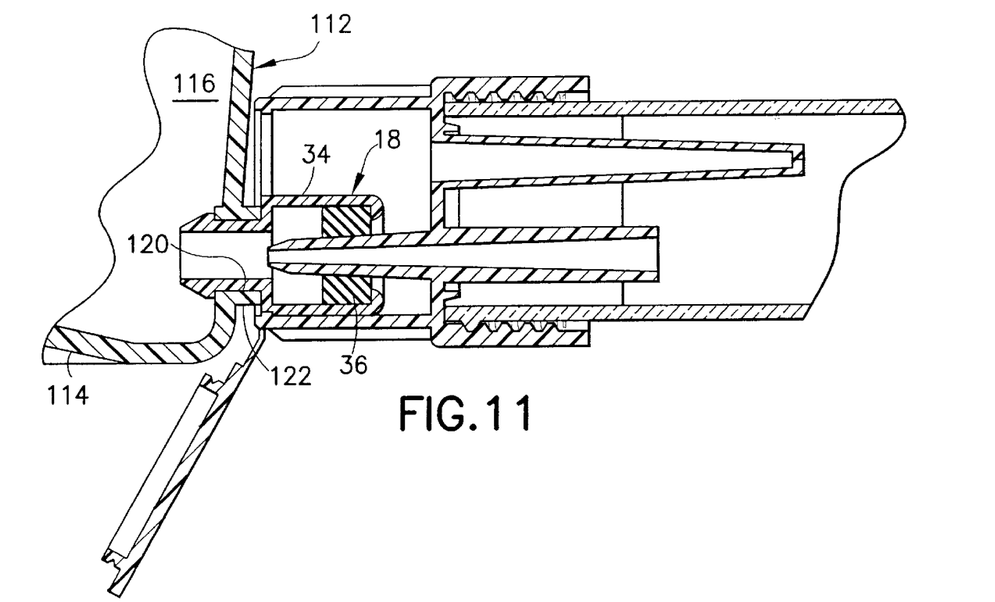
FIG. 11 is a cross-sectional view taken along line 11—11 in FIG. 10.

FIGS. 1–3 and 8 show a collection container having an outlet aperture and an access port assembly centrally mounted in a bottom wall. However, such a disposition is not required. For example, with reference to FIGS. 9–11, access port assembly 18, as described above, is employed with a container 112. Container 112 includes a bottom wall 114, a frustum-shaped side wall 116, and an open top 118. Portions of side wall 116 adjacent bottom wall 114 are provided with an outlet aperture 120. An outlet nipple 122 projects from side wall 116 and surrounds aperture 118. Access port assembly 34 is mounted to container 112 substantially as described above. Additionally, the above-described assembly of test tube 14 and cap 16 are used precisely as explained above to access the fluid in container 112.

What is claimed is:

1. A specimen collection device for collecting bodily fluids comprising:

a container having a substantially closed bottom, a bottom end, an open top and a side wall extending between said bottom end and said top;

an outlet aperture extending through portions of said container in proximity to said closed bottom; and a split septum formed from a resilient elastomeric material and having a slit extending therethrough, said split septum being sealingly secured under compression in said outlet aperture such that resiliency of said septum seals said septum at said slit therein, and said container is accessible by urging a blunt cannula through said slit in said split septum for withdrawing a portion of a fluid specimen in said container.

2. The specimen collection device of claim 1, wherein said split septum is resiliently retained in a generally tubular mounting collar, said mounting collar having mounting structure thereon for secure mounting with portions of said container surrounding said outlet aperture.

3. The specimen collection device of claim 2, wherein said mounting structure of said mounting collar comprises a substantially conical barb having a locking shoulder, said barb being configured for deflecting portions of said container adjacent said outlet aperture during insertion of said mounting collar through said outlet aperture, said locking shoulder engaging interior portions of said container adjacent said outlet aperture after sufficient insertion of said mounting collar into said outlet aperture for permanently locking said mounting collar and said split septum in said outlet aperture.

4. The specimen collection device of claim 1, further comprising a lid removably retained across said open top of said container.

5. The specimen collection device of claim 1, wherein said closed bottom includes a bottom wall extending continuously across said side wall of said container at locations between said bottom end and said open top of said container, said bottom wall being dished and having said outlet aperture extending centrally through said dished bottom wall at locations spaced upwardly from said bottom end of said container.

6. The specimen collection device of claim 1, wherein said outlet aperture is formed on portions of said side wall in proximity to said bottom wall.

7. A specimen collection device for collecting bodily fluids comprising:

a container having a bottom wall, a side wall extending upwardly from said bottom wall, a bottom end, and an open top, an outlet aperture extending through said container at a location spaced from said open top;

a split septum sealingly engaged in said outlet aperture, said split septum having a slit extending entirely therethrough, portions of said septum on opposite sides of said slit being sealingly engaged with one another;

a test tube having a closed bottom, an open top and a side wall extending therebetween; and a cap securely mounted to said side wall of said test tube adjacent said open top, said cap including a cylindrical cover wall, and a transverse wall which extends across said open top of said test tube and having an inlet aperture eccentric to and extending through said transverse wall, an upper inlet conduit registered with and communicating with said inlet aperture and extending upwardly from and eccentric to said transverse wall, said upper inlet conduit having a substantially blunt end spaced from said transverse wall and dimensioned for movement through said slit of said split septum for placing said test tube in communication with said container.

8. The specimen collection device of claim 7, further comprising a generally tubular mounting collar securely mounted in said outlet aperture of said container, said split septum being securely mounted within said mounting collar.

9. The specimen collection device of claim 8, wherein the mounting collar includes a large diameter septum retaining end portion, a small diameter mounting portion and a frustum-shaped mounting barb, said small diameter mounting portion being disposed in said outlet aperture of said container, said mounting barb being disposed in said container and engaging portions of said container adjacent said outlet aperture, said large diameter septum retaining portion being securely engaged against outer surface portions of said container adjacent said outlet aperture.

10. The specimen collection device of claim 7, further comprising a lid removably attached to said open top of said side wall of said container.

11. The specimen collection device of claim 7, wherein said outlet aperture is formed in said bottom wall of said container.

12. The specimen collection device of claim 7, wherein said outlet aperture is formed through a portion of said side wall of said container in proximity to said bottom wall thereof.

13. The specimen collection device of claim 7, wherein said cap is unitarily molded from a plastic material and includes a cover for selectively and permanently covering said cylindrical cover wall.

14. The specimen collection device of claim 13, wherein said cover is hingedly connected to said cylindrical cover wall and being hingedly rotated into sealing engagement with said cylindrical cover wall.

15. The specimen collection device of claim 7, wherein said inlet conduit includes a tapered end spaced from said transverse wall.

16. The specimen collection device of claim 7, wherein said transverse wall includes a vent aperture and a vent conduit within communication thereto, said vent conduit having a taper such that inside diameter of said vent conduit planar to said transverse wall is larger than the size of inside diameter of said vent conduit below said transverse wall.

17. The specimen collection device of claim 16, wherein said vent conduit includes a bottom wall, said bottom wall forming a narrow slit for venting air through said vent aperture.

18. The specimen collection device of claim 17, wherein said bottom wall of said vent conduit is movable such that the distance from said bottom wall to said closed bottom of said test tube is adjustable in order to selectively elect the amount of fluid to be transferred from said container to said test tube.

19. The specimen collection device of claim 17, wherein said narrow slit has a diameter that allows passage of air and prevents passage of fluid.

20. The specimen collection device of claim 17, wherein said bottom wall of said vent conduit is unitarily molded from a plastic material to said vent conduit.

21. The specimen collection device of claim 7, wherein said transverse wall further includes a vent aperture and a vent conduit within communication thereto, said vent conduit includes a bottom wall, said bottom wall forming a narrow slit for venting air through said vent aperture, said narrow slit having a diameter that allows air passage and prevents fluid passage, said bottom wall is movable such that the distance from said bottom wall to said closed bottom of said test tube is adjustable in order to selectively elect the amount of fluid to be transferred for said container to said test tube.

22. A method for collecting a urine specimen, said method comprising the steps of:

providing a container having a substantially closed bottom, an open top and a plurality of side walls extending therebetween, an outlet aperture being formed in said container in proximity to said closed bottom, a split septum being securely and sealingly retained in said outlet aperture;

collecting a sample of urine in said container;

providing a test tube having a closed bottom, an open top and a side wall extending therebetween, a cap secured to said open top of said test tube and having a blunt cannula extending therefrom and into communication with interior portions of said test tube;

urging said blunt cannula through said split septum for permitting a flow of said urine specimen from said container into said test tube; and separating said test tube and said cap from said container to permit said split septum to reseal.

23. The method of claim 22, further comprising the step of sealing said blunt cannula of said cap on said test tube after separation of said cap and said test tube from said container.

24. The method of claim 22, further comprising the step of placing a lid over said open top of said container after placing said urine specimen therein.

* * * * *